United States Patent
Bjornson et al.

[19]

[11] Patent Number: 6,103,199
[45] Date of Patent: Aug. 15, 2000

[54] CAPILLARY ELECTROFLOW APPARATUS AND METHOD

[75] Inventors: Torleif Ove Bjornson, Gilroy; Randy M. McCormick, Santa Clara; David S. Soane, Piedmont, all of Calif.

[73] Assignee: ACLARA Biosciences, Inc., Mountain View, Calif.

[21] Appl. No.: 09/153,566

[22] Filed: Sep. 15, 1998

[51] Int. Cl.⁷ ..................................................... B01L 3/02
[52] U.S. Cl. ........................... 422/100; 422/68.1; 422/70; 435/288.4; 435/288.5; 204/450; 204/453; 204/600; 204/604
[58] Field of Search ........................ 422/100, 68.1, 422/70; 435/287.1, 287.2, 288.4, 288.5; 73/863.32, 863.31, 864, 864.01; 204/450, 451, 452, 453, 454, 455, 600, 601, 602, 603, 604, 605

[56] References Cited

U.S. PATENT DOCUMENTS

| | | | |
|---|---|---|---|
| 4,237,224 | 12/1980 | Cohen et al. | 435/69.1 |
| 4,271,139 | 6/1981 | Hart | 436/531 |
| 4,382,074 | 5/1983 | Hart | 436/537 |
| 4,626,509 | 12/1986 | Lyman | 435/283.1 |
| 4,675,300 | 6/1987 | Zare et al. | 204/452 |
| 4,925,629 | 5/1990 | Schramm | 422/82.05 |
| 4,927,604 | 5/1990 | Mathus et al. | 422/101 |
| 4,965,049 | 10/1990 | Lillig et al. | 422/68.1 |
| 5,006,210 | 4/1991 | Yeung et al. | 204/452 |
| 5,043,215 | 8/1991 | Nakane et al. | 428/378 |
| 5,091,652 | 2/1992 | Mathies et al. | 250/458.1 |
| 5,104,621 | 4/1992 | Pfost et al. | 422/67 |
| 5,108,704 | 4/1992 | Bowers et al. | 422/70 |

(List continued on next page.)

FOREIGN PATENT DOCUMENTS

| | | |
|---|---|---|
| 96100072 | 7/1996 | European Pat. Off. . |
| WO 89/10977 | 4/1989 | WIPO . |
| WO 97/01755 | 1/1997 | WIPO . |
| WO 97/15394 | 5/1997 | WIPO . |

OTHER PUBLICATIONS

Baba X et al, *Trends in Anal Chem* (1992) 11:280–287.
Huang XC et al, *Anal Chem* (1992) 64:967–972.
Huang XC et al, *Anal Chem* (1992) 64:2149–2154.
Trainor GL, *Anal Chem*(1990) 62:418–426.
Anazawa, et al, *Electrophoresis* (1993) v.20, n.3: 539–546. (abstract only).
Takahashi, et al, *Anal. Chem.* (1994) v.66, n.7: 1021–1026. (abstract only).
Shiomi, et al, *J. High Resolut. Chromatogr.* (1991) v.14, n.11: 729–737. (abstract only).

(List continued on next page.)

*Primary Examiner*—Jill Warden
*Assistant Examiner*—John S. Starsiak, Jr.
*Attorney, Agent, or Firm*—Bertram I. Rowland; Rae-Venter Law Group, P.C.

[57] ABSTRACT

The present invention concerns an apparatus for conducting a microfluidic process. The apparatus comprises integral first and second plates. The first plate comprises an array of sample receiving elements for receiving a plurality of samples from an array of sample containers and dispensing the samples. The second plate comprises a planar array of microfluidic networks of cavity structures and channels for conducting a microfluidic process. Also disclosed is a method for processing an array of samples. At least a portion of each sample in an array of sample wells is simultaneously transferred to a corresponding array of microfluidic networks of cavity structures and channels by means of a corresponding array of sample receiving elements that is in integral fluid communication with the array of microfluidic networks. The samples are then processed. Also disclosed is a device for conducting a microfluidic process wherein the device comprising a planar substrate having a planar array of microfluidic networks of cavity structures and channels for conducting a microfluidic process. A plurality of such devices may be present on a continuous sheet. The invention further includes kits for carrying out microfluidic processes comprising an apparatus as described above.

17 Claims, 4 Drawing Sheets

U.S. PATENT DOCUMENTS

| | | | |
|---|---|---|---|
| 5,120,414 | 6/1992 | Carson et al. | 204/453 |
| 5,171,531 | 12/1992 | Christianson et al. | 422/64 |
| 5,188,148 | 2/1993 | Garrison | 137/606 |
| 5,202,231 | 4/1993 | Drmanac et al. | 435/6 |
| 5,213,766 | 5/1993 | Flesher et al. | 422/102 |
| 5,219,528 | 6/1993 | Clark | 422/101 |
| 5,252,743 | 10/1993 | Barrett et al. | 548/303.7 |
| 5,274,240 | 12/1993 | Mathies et al. | 250/458.1 |
| 5,277,780 | 1/1994 | Kambara | 204/603 |
| 5,286,652 | 2/1994 | James et al. | 436/48 |
| 5,324,401 | 6/1994 | Yeung et al. | 204/452 |
| 5,325,889 | 7/1994 | Paul et al. | 137/594 |
| 5,332,480 | 7/1994 | Datta et al. | 204/451 |
| 5,338,427 | 8/1994 | Shartle et al. | 204/604 |
| 5,356,525 | 10/1994 | Goodale et al. | 204/602 |
| 5,372,695 | 12/1994 | Demorest | 204/603 |
| 5,384,093 | 1/1995 | Ootani et al. | 422/63 |
| 5,413,686 | 5/1995 | Klein et al. | 204/603 |
| 5,439,578 | 8/1995 | Dovichi et al. | 204/603 |
| 5,455,008 | 10/1995 | Earley et al. | 422/100 |
| 5,463,910 | 11/1995 | Burns et al. | 73/864.21 |
| 5,525,302 | 6/1996 | Astle | 422/100 |
| 5,560,811 | 10/1996 | Briggs et al. | 204/451 |
| 5,585,277 | 12/1996 | Bowie et al. | 436/518 |
| 5,589,330 | 12/1996 | Shuber | 435/5 |
| 5,599,695 | 2/1997 | Pease et al. | 435/91.1 |
| 5,631,734 | 5/1997 | Stern et al. | 356/317 |
| 5,637,509 | 6/1997 | Hemmila et al. | 436/537 |
| 5,730,850 | 3/1998 | Kambara et al. | 204/603 |
| 5,833,827 | 11/1998 | Anazawa et al. | 204/603 |
| 5,855,430 | 3/1999 | Kernan et al. | 204/453 |
| 5,872,010 | 2/1999 | Karger et al. | 422/100 |
| 5,938,908 | 8/1999 | Anazawa et al. | 204/603 |
| 5,968,331 | 10/1999 | Kambara et al. | 204/450 |

OTHER PUBLICATIONS

Kamahori, et al, *Japanese Journal of Electrophoresis* (1997) v.41, n.6: 313–318. (abstract only).

Anazawa, et al, *Anal. Chem.* (1996) v.68 n.15: 2699–2704. (abstract only).

Adam T. Woolley and Richard A. Mathies, "Ultra–high Speed DNA Fragment Separations Using Microfabricated Capillary Array Electrophoresis Chips" Proceedings of the National Academy of Sciences, USA vol. 91 (Nov. 1994) 11348–11352.

Woodley, et al, *Proc. Natl. Acad. Sci. USA.* (1994) v.9, 11348–52.

Jacobson, et al, *Anal. Chem.* (1994) v.66, n.7: 1107–13.

CAPILLARY ELECTROFLOW APPARATUS AND METHOD

BACKGROUND OF THE INVENTION

1. Field of the Invention

This invention relates generally to the receiving and dispensing of samples such as in the field of separation of biomolecules and, in particular, separations by capillary electrophoresis and the use of the capillary electrophoresis to detect such biomolecules.

In a range of technology-based business sectors, including the chemical, bioscience, biomedical, and pharmaceutical industries, it has become increasingly desirable to develop capabilities for rapidly and reliably carrying out chemical and biochemical reactions in large numbers using small quantities of samples and reagents. Carrying out a massive screening program manually, for example, can be exceedingly time-consuming, and may be entirely impracticable where only a very small quantity of a key sample or component of the analysis is available, or where a component is very costly.

Accordingly, considerable resources have been directed to developing methods for high-throughput chemical synthesis, screening, and analysis. Subsequently, considerable art has emerged, in part, from such efforts. Automated laboratory workstations have contributed significantly to advances in pharmaceutical drug discovery and genomics over the past decade. See for example, U.S. Pat. Nos. 5,104,621 and 5,356,525 (Beckman Instruments). More specifically, robotics technology has played a major role in providing a practical useful means for enabling high throughput screening (AS) methods. Reference can be made to U.S. Pat. No. 4,965,049.

In addition to the emergence of automation technology, the last decade has seen an enormous advance in the scientific understanding of critical cellular processes, and this has led to rationally designed approaches in drug discovery. Also, the application of molecular genetics and recombinant DNA technology, U. S. Pat. No. 4,237,224 (Cohen and Boyer), has led to the isolation of many genes encoding proteins which show promise as targets for new drugs. Once a target gene is identified, the recombinant protein can be heterologously expressed in mammalian tissue culture cells, insect cells, bacteria and/or yeast.

The advantages of employing molecular cloning methodologies techniques are many. Often receptors and enzymes exist in alternative forms, subtypes or isoforms. Using a cloned target focuses the primary screen on the subtype appropriate for the disease. Agonists or antagonists can be identified and their selectivity can then be tested against the other known subtypes. The availability of such cloned genes and corresponding expression systems have enabled new types of screens to be created that are specific, sensitive, and often automatable. Matched with the scientific and technological advances in biology has been the emergence of innovative methods for highly parallel chemical synthesis. For several decades, preparation of synthetic analogs to the prototypic lead compound was the established method for drug discovery. Natural products were usually isolated from soil microbes and cultured under a wide variety of conditions. The spectrum of organisms employed by the pharmaceutical industry for isolation of natural products has now expanded from actinomycetes and fungi to include plant, marine organisms, and insects During the last five years, the chemistry of creating combinatorial libraries has made a vastly increased number of synthetic compounds available for testing. More specifically, thousands to tens or hundreds of thousands of small molecules can be rapidly and economically synthesized. See, for example, the combinatorial chemistry patents (U.S. Pat. No. 5,252,743 (Affymax Technologies N.V.). Thus, combinatorial libraries complement the large numbers of synthetic compounds available from the more traditional drug discovery programs based, in part, on identifying lead compounds through natural product screening.

Competitive binding assays, originally developed in the 1960's for immunodiagnostic applications, continue to be commonly employed for quantitatively characterizing receptor-ligand interactions. Despite advances in the development of spectrophotometric and fluorometric-based bioanalytical assays, radiolabeled ligands are still commonly employed in pharmaceutical HTS applications. Although non-isotopic markers promise to be environmentally cleaner, safer, less expensive, and generally easier to use than radioactive compounds, sensitivity limitations have prevented these new methods from becoming widespread. Another major disadvantage of the competition assay is the number of steps, most notably, washing steps, required to run the screen.

A few years ago, Scintillation Proximity Assays were introduced by Amersham and also are discussed in U.S. Pat. Nos. 4,271,139 and 4,382,074 as a means of circumventing the wash steps required in the above heterogeneous assays The new homogeneous assay technology, which requires no separation of bound from free ligand, is based on the coating of scintillant beads with an acceptor molecule, for example, the target receptor.

Another variation of this theme avoids the use of radioactivity and is especially useful in high-throughput assays The modification involves the use of lanthanide chelates in time-resolved fluorometry. Aspects of this particular homogeneous assay technology are discussed in U.S. Pat. No. 5,637,509. This particular technology takes advantage of the unique properties of the lanthanide chelate europium-cryptate in combination with the energy-absorbing molecule, allophycocyanin (APC).

Robotic-based high-throughput tools are now routinely used for screening libraries of compounds for the purpose of identifying lead molecules for their therapeutic potential. Subsequently, considerable art has emerged. For example, PerSeptive Biosystems' screening method for characterizing ligand binding to a given target employs a variety of separation techniques and is described filer in the PCT application WO 97/01755. Another related method is described in U.S. Pat. No. 5,585,277 (Scriptgen Pharmaceuticals).

Highly parallel and automated methods for DNA synthesis and sequencing have also contributed significantly to the success of the human genome project to date. For DNA synthesis instrumentation, see, e.g., PE/Applied Biosystems (ABI), PerSeptive BioSystems, Pharmacia Biotech, and Beckman Instruments. For DNA sequencing, see, e.g., ABI and LiCor. In addition, see U.S. Pat. No. 5,455,008. For a related invention, see Genzyme Corporation's HTS method for DNA analysis that is described in U.S. Pat. No. 5,589,330. For sequencing by hybridization, see PCT WO 89/10977 (Southern), Affymetrix (U.S. Pat. Nos. 5,599,695 and 5,631,734), and U.S. Pat. No. 5,202,231 (Drmanac, et al.).

Computerized data handling and analysis systems have also emerged with the commercial availability of high-throughput instrumentation for numerous life sciences research and development applications. Commercial software, including database and data management software, has become routine in order to efficiently handle the large amount of data being generated. Bioinformatics has emerged as an important field.

With the developments outlined above in molecular and cellular biology, combined with advancements in combinatorial chemistry, have come an exponential increase in the number of targets and compounds available for screening. In addition, many new genes and their expressed proteins will be identified by the Human Genome project and will therefore greatly expand the pool of new targets for drug discovery. Subsequently, an unprecedented interest has arisen in the development of more efficient ultra-high throughput methods and instrumentation for pharmaceutical and genomics screening applications. In recent parallel technological developments, miniaturization of chemical analysis systems, employing semiconductor processing methods, including photolithography and other wafer fabrication techniques borrowed from the microelectronics industry, has attracted increasing attention and has progressed rapidly. The so-called "lab-chip" technology enables sample preparation and analysis to be carried out onboard microfluidic-based cassettes. Moving fluids through a network of interconnecting enclosed microchannels of capillary dimensions is possible using electrokinetic transport methods.

Application of microfluidics technology embodied in the form of analytical devices has many attractive features for pharmaceutical high throughput screening. Advantages of miniaturization include greatly increased throughput and reduced costs, in addition to low consumption of both sample and reagents and system portability. Implementation of these developments in microfluidics and laboratory automation holds great promise for contributing to advancements in life sciences research and development.

Nonetheless, the 96 well microtiter plate has and still is the pharmaceutical industry standard for carrying out bio-analytical assays despite the recent advances in miniaturization and microfluidics. Because an enormous number of synthetic libraries have and continue to be generated using this particular multiwell format, the microtiter plate will remain entrenched within the industry.

Automated workstations for drug discovery and genomics applications are not capable of incorporating microfluidic multi-assay cards into existing robotic based high throughput microtiter plate handling and assay systems. Thus, as microfluidic technologies advance, new methods for enabling fluid transfer between multi-well plates and microassay cassettes would be beneficial. A critical factor currently limiting such a microfluidic HTS hybrid device is a means for reproducible liquid communication between the disparate dimensions of the two systems. More specifically, integration of microfluidics technology with existing robotic-based methods currently used in automated workstations is constrained by differences in volume size of samples used. For these reasons, new automated methods for multiplexing common lab tasks such as sample handling and dispensing on the microscale is required.

Capillary-based separations are widely used for analysis of a variety of analyte species. Numerous subtechniques, all based on electrokinetic-driven separations, have been developed. Capillary electrophoresis is one of the more popular of these techniques and can be considered to encompass a number of related separation techniques such as capillary zone electrophoresis, capillary gel electrophoresis, capillary isoelectric focusing, capillary isotachophoresis, and micellar electrokinetic chromatography. In the context used throughout this application, the phrase "capillary electrophoresis" is used to refer to any and all of the aforementioned electrokinetic separation subtechniques.

Electrophoresis is a separation process in which molecules with a net charge migrate through a medium under the influence of an electric field. Traditionally, slab gel electrophoresis has been a widely used tool in the analysis of genetic materials. See, for example, G. L. Trainor, Anal. Chem. (1990) 62:418–26. Capillary electrophoresis has emerged as a powerful separation technique with applicability to a wide range of molecules from simple atomic ions to large DNA fragments. In particular, capillary electrophoresis has become an attractive alternative to slab electrophoresis for biomolecule analysis, including DNA sequencing. See, for example, Y. Baba, et al., Trends in Anal. Chem. (1992) 11:280–287. This is generally because the small size of the capillary greatly reduces Joule heating associated with the applied electrical potential. Furthermore, capillary electrophoresis requires less sample and produces faster and better separations than slab gels.

Currently, sophisticated experiments in chemistry and biology, particularly molecular biology, involve evaluating large numbers of samples. For example, DNA sequencing of genes is time consuming and labor intensive. In the mapping of the human genome, a researcher must be able to process a large number of samples on a daily basis. If capillary Enelectrophoresis can be conducted and monitored simultaneously on many capillaries, i.e., multiplexed, the cost and labor for such projects can be significantly reduced. Attempts have been made to sequence DNA in slab gels with multiple lanes to achieve multiplexing. However, slab gels are not readily amenable to a high degree of multiplexing and automation.

Difficulties exist in preparing uniform gels over a large area, maintaining gel to gel reproducibility and loading sample wells. Furthermore, difficulties arise as a result of the large physical size of the separation medium, the requirements for uniform cooling, large amounts of media, buffer, and samples, and long run times for extended reading of nucleotide sequences. Unless capillary electrophoresis can be highly multiplexed and multiple capillaries run in parallel, the advantages of capillary electrophoresis cannot produce substantial improvement in shortening the time needed for sequencing the human genome.

Capillary electrophoresis possesses several characteristics which makes it amenable to this application. The substantial reduction of Joule heating per lane makes the overall cooling and electrical requirements more manageable. The cost of materials per lane is reduced because of the smaller sample sizes. The reduced band dimensions are ideal for excitation by laser beams, as well as focused broad band sources, and for imaging onto array detectors or discrete spot detectors. The concentration of analyte into such small bands results in high sensitivity. The use of electromigration injection, i.e., applying the sample to the capillary by an electrical field, provides reproducible sample introduction with little band spreading, minimal sample consumption, and little labor.

Among the techniques used for detecting target species in capillary electrophoresis, laser-excited fluorescence detection so far has provided the lowest detection limits. Therefore, fluorescence detection has been used for the detection of a variety of analyses, especially macromolecules, in capillary electrophoresis. There have been attempts to implement the analysis of more than one capillary simultaneously in the electrophoresis system, but the number of capillaries has been quite small. For example, S. Takahashi, et al., Proceedings of Capillary Electrophoresis Symposium, December, 1992, referred to a multicapillary electrophoresis system in which DNA fragment samples were analyzed by laser irradiation causing fluorescence. This method, however, relies on a relatively poor focus (large focal spot) to allow coupling to only a few capillaries. Thus, this method could not be applied to a large number of capillaries. This method also results in relatively low intensity and, thus, poor sensitivity because of the large beam. Furthermore, detection in one capillary can be influenced by light absorption in the adjacent capillaries, thus affecting accuracy due to cross-talk between adjacent capillaries.

Attempts have been made to perform parallel DNA sequencing runs in a set of up to 24 capillaries by providing laser-excited fluorometric detection and coupling a confocal illumination geometry to a single laser beam and a single photomultiplier tube. See, for example, X. C. Huang, et al., Anal. Chem. (1992) 64:967–972, and Anal. Chem. (1992) 64:2149–2154. Also see U.S. Pat. No. 5,274,240. However, observation is done one capillary at a time and the capillary bundle is translated across the excitation/detection region at 20 mm/see by a mechanical stage.

There are features inherent in the confocal excitation scheme that limit its use for very large numbers of capillaries. Because data acquisition is sequential and not truly parallel, the ultimate sequencing speed is generally determined by the observation time needed per DNA band for an adequate signal-noise ratio. Moreover, the use of a translational stage can become problematic for a large capillary array. Because of the need for translational movement, the amount of cycling and therefore bending of the capillaries naturally increases with the number in the array. It has been shown that bending of the capillaries can result in loss in the separation efficiency. This is attributed to distortions in the gel and multipath effects. Sensitive laser-excited fluorescence detection also requires careful alignment both in excitation and in light collection to provide for efficient coupling with the small inside diameter of the capillary and discrimination of stray light. The translational movement of the capillaries thus has to maintain stability to the order of the confocal parameter (around 25 ~m) or else the cylindrical capillary walls will distort the spatially selected image due to misalignment of the capillaries in relation to the light source and photodetector. In addition, long capillaries provide slow separation, foul easily, and are difficult to replace.

2. Previous Disclosures

U.S. Pat. No. 5,324,401 to Young, et al., describes a multiplexed capillary electrophoresis system where excitation light is introduced through an optical fiber inserted into the capillary. In this system the capillaries remain in place, i.e. in the buffer solutions when the capillaries are read.

U.S. Pat. No. 5,332,480 (Datta, et al.) describes a multiple capillary electrophoresis device for continuous batch electrophoresis.

U.S. Pat. No. 5,277,780 (Kambara) describes a two dimensional capillary electrophoresis apparatus for use with a two dimensional array of capillaries for measuring samples, such as DNA samples, in an array of test wells.

U.S. Pat. 5,413,686 (Klein and Miller) describes a multi-channel automated capillary electrophoresis analyzer in which multiple individual separation capillaries are installed in a instrumental analyzer which serves to flush and fill the capillaries and associated buffer reservoirs from supplies of buffer situated within the instrument.

U.S. Pat. 5,439,578 (Dovichi and Zhang) describes a multiple capillary biochemical analyzer based on an array of separation capillaries terminating in a sheath flow cuvette. The use of the sheath flow cuvette facilitates detection of the analyte bands by reducing the magnitude of scattered radiation from the detection zone.

U.S. Pat. No. 5,338,427 (Shartle, et al.) describes a single use capillary cartridge having electrically conductive films as electrodes; the system does not provide for multiplexed sampling, sample handling, and electrophoresis.

U.S. Pat. Nos. 5,091,652 (Mathies, et al.) and 4,675,300 (Zare, et al.) describe means for detecting samples in a capillary.

U.S. Pat. No. 5,372,695 (Demorest) describes a system for delivering reagents to serve a fix capillary scanner system.

Numerous examples of sample handling for capillary electrophoresis are known. For example, James in U.S. Pat. No. 5,286,652 and Christianson in U.S. Pat. No. 5,171,531 are based on presenting a single vial of sample to a single separation capillary for a sequential series of analyses.

Goodale in U.S. Pat. No. 5,356,525 describes a device for presentation of a tray of 7 vials of samples to an array of seven capillaries for the sample injection process.

Carson in U.S. Pat. No. 5,120,414 describes injection of a sample contained within a porous membrane onto a single capillary electrophoresis device. The end of the capillary must be in intimate contact with the porous membrane to effect sample introduction into the capillary. In contrast, the present invention provides short disposable capillaries mounted in a frame that is integral with a liquid handling system. This system permits a rapid multiplexed approach to capillary electrophoresis.

Numerous examples of multi-well devices with integral membranes are known (e.g., Mann in U.S. Pat. No. 5,043, 215, Matthis in U.S. Pat. No. 4,927,604, Bowers in U.S. Pat. No. 5,108,704, Clark in U.S. Pat. No. 5,219,528). Many of these devices attach to a base unit, which can be evacuated, drawing samples through the membrane for filtration.

Numerous examples of multi-channel metering devices such as multi channel pipettes are known. One example is described in a device by Schramm in U.S. Pat. No. 4,925, 629, which utilizes an eight channel pipette to meter samples/reagents to/from multi-well plates. A second example is a 96 channel pipetting device described by Lyman in U.S. Pat. No. 4,626,509. These devices use positive displacement plungers in corresponding cylinders to draw in and expel liquid in the sampling/metering step.

Flesher in U.S. Pat. No. 5,213,766 describes a 96 channel device which contains flexible "fingers" which can be deformed out of a common plane; each "finger" can be deflected into a well of a multi-well plate to acquire a small aliquot of sample by one of several mechanisms.

Zare, et al., (U.S. Pat. No. 4,675,300) discusses a fluoroassay method for the detection of macromolecules such as genetic materials and proteins by capillary electrophoresis.

Yeung, et al., (U.S. Pat. No. 5,006,210) presented a system for capillary zone electrophoresis with indirect laser-induced fluorescence detection of macromolecules, including proteins, amino acids, and genetic materials. Systems such as these generally involve only one capillary.

U.S. Pat. Nos. 5,188,148 for a conduit plate for fluid delivery system and U.S. Pat. No. 5,325,889 for a laminated conduit plate for fluid delivery system both issued to Millipore Corp.

U.S. Pat. No. 5,463,910 discloses a multi-function aspirating device (AVL Scientific Corp.) U.S. Pat. No. 5,384,093 discusses an apparatus for aspirating and discharging a liquid sample (Toa Medical Electronics Co., Ltd.).

U.S. Pat. No. 5,525,302 discloses a method and device for simultaneously transferring plural samples.

A multiwell plate is disclosed in PCT WO 97/15394 published May 1, 1997 (SmithKline Beecham Corporation). The wells have a large opening at the top and small nozzle hole in the base. The opening is chosen so that a jet of liquid is emitted when a pressure pulse is applied to the surface such that by selecting a time for the pressure pulse a precise amount of volume in the well can be dispensed.

SUMMARY OF INVENTION

One aspect of the present invention concerns an apparatus for conducting a microfluidic process. The apparatus comprises integral first and second plates. The first plate comprises an array of sample receiving elements for receiving and/or dispensing a plurality of samples from an array of sample containers. The second plate comprises a planar array of microfluidic networks of cavity structures and channels for conducting a microfluidic process.

In another aspect the apparatus for conducting a microfluidic process comprises a first plate comprising an array of sample receiving elements adapted for receiving and/or dispensing a plurality of samples from an array of sample wells. The apparatus also comprises a second plate integral with the first plate. The second plate comprises a planar array of microfluidic networks of cavity structures and channels for conducting a microfluidic process. Each of the microfluidic networks is adapted for fluid communication with a corresponding sample receiving element.

Another aspect of the present invention is a method for processing an array of samples. At least a portion of each sample in an array of sample wells is simultaneously transferred to a corresponding array of microfluidic networks of cavity structures and channels by means of a corresponding array of sample receiving elements that are adapted for fluid communication with a corresponding sample receiving element of said first plate. The samples are then processed.

Another aspect of the present invention is a method for processing an array of samples. At least a portion of each sample in an array of sample wells is simultaneously transferred to a corresponding array of sample receiving elements. At least a portion of each sample is simultaneously transferred from the sample receiving elements to a corresponding array of microfluidic networks that are adapted for fluid communication with a corresponding sample receiving element. The array of samples is then processed.

Another aspect of the present invention is a method for processing an array of samples. In this embodiment at least a portion of each sample in an array of sample wells is simultaneously transferred to a corresponding array of sample receiving elements that are part of a first plate comprising an array of sample receiving elements adapted for receiving a plurality of samples from an array of sample wells. At least a portion of each sample from the sample receiving elements is simultaneously transferred to a corresponding array of microfluidic networks that is part of a second plate integral with the first plate. The second plate comprises a planar array of microfluidic networks of cavity structures and channels for conducting a microfluidic process. Each of the microfluidic networks is adapted for fluid communication with a corresponding sample receiving element. The samples are then processed.

Another aspect of the present invention comprises kits for processing a sample. The kit comprises an apparatus as described above and reagents, other than reagents within the apparatus, for processing a sample.

Another aspect of the present invention is a method for analysis of an array of samples in an array of sample containers by capillary electrophoresis. An array of samples in an array of sample containers is provided. At least a portion of each sample in the array of sample containers is simultaneously transferred to a corresponding array of capillary electrophoresis columns. Separation of the transferred samples is simultaneously conducted by capillary electrophoresis. The capillary electrophoresis separations are then analyzed.

Another aspect of the present invention is a method for analysis of an array of samples in an array of sample Hcontainers by capillary electrophoresis. An array of aliquots of sample is acquired simultaneously from an array of samples in sample containers. The array of samples is simultaneously processed to provide an array of processed samples. The array of processed samples is simultaneously transferred for capillary electrophoresis to an array of capillary electrophoresis columns. Capillary electrophoresis is simultaneously conducted on the array of the capillary electrophoresis columns and the columns are analyzed. The invention encompasses a system for multiplexing capillary electrophoresis analysis of multiple samples comprising:

a) means for simultaneously acquiring an array of aliquots of sample from an array of samples in sample containers;

b) means, in combination with means (a), for simultaneously processing the array of samples to provide an array of processed samples and presenting the array of processed samples for capillary electrophoresis;

c) means for simultaneously transferring an array of processed samples to an array of capillary electrophoresis columns;

d) means for simultaneously conducting capillary electrophoresis on the array of the capillary electrophoresis columns from (c); and e) means for analyzing capillary electrophoresis columns from (d).

Another aspect of the present invention is a device for conducting a microfluidic process wherein the device comprises a planar substrate having a planar array of microfluidic networks of cavity structures and channels for conducting a microfluidic process.

Another aspect of the present invention is a method for securing an array of samples. At least a portion of each sample in an array of sample wells of a multiwell plate is simultaneously transferred to a corresponding array of sample receiving elements. At least a portion of each sample from the sample receiving elements is simultaneously transferred to a corresponding array of sample handling wells.

Another aspect of the present invention is a method for securing an array of samples wherein at least a portion of each sample in an array of sample wells of a multiwell plate is simultaneously transferred to a corresponding array of sample receiving elements. At least a portion of each sample from the sample receiving elements is simultaneously transferred to a corresponding array of sample handling wells. The portion of each sample is expelled from the sample receiving elements by application of an electric field or application of pressure.

Another aspect of the present invention is a method for processing an array of samples that comprises:

(a) simultaneously transferring at least a portion of each sample in an array of sample wells to a corresponding array of sample receiving elements, (b) simultaneously transferring at least a portion of each sample from the sample receiving elements to a corresponding array of microfluidic networks that is in integral fluid communication with the sample receiving elements wherein the portion is expelled from the sample receiving elements by application of an electric field or application of pressure, and (c) processing the array of samples.

DESCRIPTION OF THE SPECIFIC EMBODIMENTS

Figure 1:
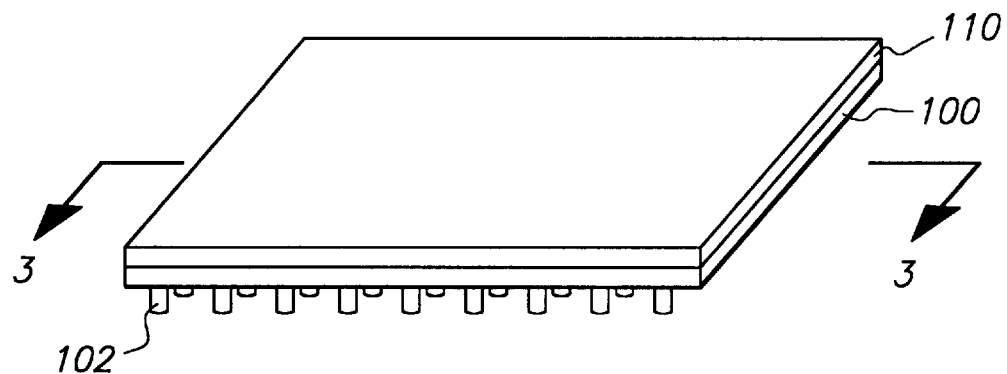
FIG. 1 is a perspective view of one embodiment of an apparatus in accordance with the present invention.

The present invention encompasses methods and apparatus for simultaneously transferring samples from an array of sample containers to an array of sample receiving elements, simultaneously transferring samples from said sample receiving elements to a planar array of microfluidic networks of interconnected cavity structures and channels of capillary dimensions and simultaneously conducting a microfluidic process. It is to be noted that simultaneous transfer may be from all or a portion of the array to a corresponding portion of the microfluidic networks. The miniaturized system of enrichment trenches, reaction chambers and detection zones enable multiple laboratory processes to be integrated "onboard" a planar substrate, including sample preparation, incubation, electrophoretic separations, and analyses.

The present invention differs from known procedures in microfluidic technology such as microelectrophoresis in that it provides for simultaneously sampling an array of samples; simultaneously handling the samples and presenting an array of the samples for electrophoresis; simultaneously transferring the array of presented samples to an array of capillaries; and simultaneously conducting processing of the samples in the capillary columns.

The invention has many advantages over conventional microfluidic techniques such as microelectrophoresis technology. The time period for conducting a microfluidic process is much shorter than with conventional techniques such as electrophoresis. Whereas conventional separation on gels is manually intensive, the present invention only requires sample introduction since the remaining processing is automatic. The invention system will perform confirmations in parallel. The present invention system typically requires only 1 to 5% of the amount of sample used in standard electrophoresis. The present invention system can perform a quantitative determination in a much simpler format and much shorter time period than with conventional electrophoresis. Since reactions are in the liquid phase, the invention system provides greater speed, greater specificity and less background biochemical noise and quantitation is achieved in tens of minutes instead of hours. The present invention system only requires small amounts of sample. Reagent reservoirs may have volumes ranging from 0.01 to 100 $\mu$l, more typically, 0.1 to 10 $\mu$l. Once drawn from the reservoir, sample volumes transported through the microchannels range from 1 to 1000 nanoliters, more typically, 10 to 100 nanoliters. Volumes of sample drawn for individual microinjected reaction or separation plugs are 0.01 to 10 nanoliters, more typically, 0.1 to 1 nanoliters.

Many of these advantages may be achieved in a variety of assays including immunoassays, DNA binding assays including total DNA determinations and DNA hybridizations, receptor-ligand competitive binding assays including whole cell assays, and the like. The capability to add a common reagent to multiple samples in, for example, a 96-well or a multi-well plate, mix, and react in the sample containers means that a primary reaction step (e.g. displacement of a common ligand to a receptor) can be done in discrete small volumes, in parallel with precise timing, with a minimum of carry-over and cross contamination, and without contamination of the starting material (e.g. any array or library of compounds). It is an important aspect of the present invention that simultaneous transfer may be carried out with respect to all of the wells in a multiwell plate or only with respect to some of the wells thereof. For example, one may wish to transfer samples with respect to only 8 or 16 or some other number of wells in a 96 well plate. Such transfer may be achieved by employing means for independently activating the present device to provide simultaneous transfer for less than the full number of wells in a multiwell plate.

Before proceeding further with a detailed description of the present invention, a number of terms as used herein are defined.

Array—an arrangement of a plurality of elements such as a plurality of wells in a multiwell source plate, a plurality of apertures or nozzles in a sample transfer plate, a plurality of microfluidic networks on the multi-assay card, and so forth.

Planar array—an array that is arranged in a plane, which may be the plane of an object such as, for example, a planar substrate, comprising the array. Cavity structure—an unfilled space with a mass, preferably, a hollowed out space in an object, such as, e.g., a planar substrate, a plate, or the like in accordance with the present invention such as, for example, a well, a reservoir, an incubation chamber, a separation chamber, an enrichment chamber, a detection chamber, and the like.

The cavity structures are usually present at one or both of the termini, i.e., either end, of a channel. The cavity structures may serve a variety of purposes, such as, for example, means for introducing a buffer solution, elution solvent, reagent rinse and wash solutions, and so forth into a main channel or one or more interconnected auxiliary channels, receiving waste fluid from the main channel, and the like.

Channels—a conduit or means of communication, usually fluid communication, more particularly, liquid communication, between elements of the present apparatus. The elements in communication are, e.g., cavity structures, and the like. Channels include capillaries, grooves, trenches, microflumes, and so forth. The channels may be straight, curved, serpentine, labyrinth-like or other convenient configuration within the planar substrate. The cross-sectional shape of the channel may be circular, ellipsoid, square, rectangular, triangular and the like so that it forms a microchannel within the planar substrate in which it is present.

The inside of the channel may be coated with a material for strength, for enhancing or reducing electrokinetic flow, for enhancing detection limits and sensitivity, and so forth. Exemplary of coatings is silylation, polyacrylamide (vinyl bound), methylcellulose, polyether, polyvinylpyrrolidone, and polyethylene glycol, polypropylene, Teflon™ (DuPont), Nafion™ (DuPont), and the like may also be used.

Capillary dimension—a cross-sectional area that provides for capillary flow through a channel. At least one of the cross-sectional dimensions, e.g., width, height, diameter, is at least about 1 $\mu$m, usually at least 10 $\mu$m, and is usually no more than 500 $\mu$m, preferably no more than 200 $\mu$m. Channels of capillary dimension typically have an inside bore diameter (ID) of from about 1 to 200 microns, more typically from about 25 to 100 microns.

Microfluidic—of or pertaining to fluids and being of a magnitude on the order consistent with capillary dimension.

Microfluidic network—a system of interconnected cavity structures and capillary-size channels configured with a plurality of branches through which fluids may be manipulated and processed.

Well plate—a plate comprising an array of wells. The plate may have any number of wells, which are usually in a pattern, and are usually 96, 192, 384 or 1536 well plates. Exemplary of such well plates is microtiter plates having a pattern of wells.

Integral—a single unit or a group of parts formed as a unit. Although the unit may be formed from separate parts, the parts are generally non-separable by virtue of being permanently attached or rendered integral by interlocking means. Parts in such a unit may be rendered non-separable by such processes as welding such as ultrasonic welding, the use of adhesives, gluing, bonding, sealing and the like. The components are present in a single, compact readily handled unit.

Electroflow—the manipulation of entities such as molecules, particles, cells and the like through a medium under the influence of an applied electric field by use of electrodes and the like to induce movement such as electrokinetic flow including, electroosmotic flow, electrophoretic flow, dielectrophoretic flow, and so forth. Depending on the nature of the entities, e.g., whether or not they carry an electrical charge, as well as the surface chemistry of the chamber in which the electroflow is conducted, the entities may be moved through the medium under the direct influence of the applied electric field or as a result of bulk fluid flow through the pathway resulting from the application of the electric field, e.g., electroosmotic flow. It is within the purview of the present invention that electroflow can be carried out in conjunction with movement of material by gravity or by application of a magnetic field, centrifugal force, thermal gradients, pneumatic means including negative (vacuum) and positive (pumping) pressure, and the like.

Electroflow medium—an electrically conductive medium; a medium generally utilized in carrying out electrophoretic processes. The particular medium chosen is one that is suitable to a particular application of the present invention. The medium should not interfere to any substantial degree with the electric fields used when utilizing an apparatus of the present invention. Such media include, for example, a buffer solution, cross-linked and uncross-linked polymeric solution, solvents, detergents, surfactant micellular dispersion, a gel of the type generally used in connection with analytical separation techniques, and so forth. For example, polyacrylamide gel used in PAGE analytical procedures, cellulose derivatives, polyvinyl alcohols, polyethylene oxides and the like may be used. For a discussion of such media see, e.g., Barron and Blanch, "UDNA Separations by Slab Gel and Capillary Electrophoresis: Theory and Practice," Separation and Purification Methods (1995) 24:1–118.

The electroflow medium may be a conventional buffer such as, for example, the Good's buffers (HEPES, MOPS, MES, Tricine, etc.), and other organic buffers (Tris, acetate, citrate, and formate), including standard inorganic compounds (phosphate, borate, etc.). Exemplary buffer systems include: i) 100 mM sodium phosphate, pH 7.2 ii) 89.5 mM tris-base, 89:5 mM Boric acid, 2 mM ETDA, pH 8.3. Buffer additives include methanol, metal ions, urea, surfactants, and zwitterions, intercalating dyes and other labeling reagents. Polymers can be added to create a sieving buffer for the differential separation of DNA based on fragment length. Examples of such polymers are polyacrylamide (cross-linked or linear), agarose, methylcellulose and derivatives, dextrans, and polyethylene glycol. Inert polymers can be added to the separation buffer to stabilize the separation matrix against factors such as convection mixing.

Alternatively, buffers containing micelles could be used for effecting separation of electrically neutral or hydrophobic substances of interest. The micelles are formed in the buffer by addition of an appropriate surfactant at a concentration exceeding the critical micelle concentration of that detergent. Useful surfactants include but are not limited to sodium dodecyl sulfate, dodecyltrimethyl ammonium bromide, etc. Weakly charged or apolar analyses partition into the micelles to different degrees depending upon their degree of hydrophobicity and thus can be separated. This subtechnique of capillary electrophoresis is termed micellar electrokinetic chromatography.

Electrophoresis—separation of components in a liquid by electroflow. Various forms of electrophoresis include, by way of example and not limitation, free zone electrophoresis, gel electrophoresis, isotachophoresis, high performance CE, capillary zone electrophoresis, isoelectric focusing, micellar electrokinetic capillary chromatography, and the like.

Electrophoresis column—in the context of the present invention, a channel for carrying out electrophoresis.

Processing—samples may be processed by one or more of any number of procedures such as, for example, subjecting such sample to separation procedures for sample enrichment, isolation or purification, analyzing such sample such, e.g., as an assay, detection and the like, carrying out a chemical synthesis with such sample, such as those involved with combinatorial chemistry methods for small and large molecule synthesis, and so forth. For example, polynucleotides may be synthesized or sequenced. Different nucleotides can be reacted to form DNA and different amino acids can be reacted to form proteins. These reactions can be carried out at greatly increased speeds as compared with conventional mechanical technologies. In addition to increased speeds, the yield is vastly improved due to the precision with which the reactants can be moved in accordance with the present invention.

In addition to carrying out synthesis reactions in a manner described above, it is possible to carry out DNA or protein sequencing procedures. In connection with these procedures, individual amino acids on proteins or individual nucleotides on DNA molecules can be successively cleaved from one end of the molecule. As the amino acid or nucleotide is cleaved, it can be moved to a given location within the device and identified such as by utilizing a spectrometer including spectrophotometer and spectrofluorometer. The use of such a sequencing technology obviates the need for valves, reagents, bottles, washing, filtration and many of the tedious operations that are mechanical in nature and necessary in connection with conventional sequencing methodologies.

In addition to the separation, synthesis and sequencing methods described above, the present invention is useful for a variety of additional purposes. For example, it is possible to utilize specific embodiments of the invention in order to separate impurities from large mixtures of compounds and thus carry out a purification processing which is substantially more refined than vacuum fractionation processing. A mixture of components can be separated into a variety of pure groups and moved along parallel tracks. Upon resolving the mixtures, the desired components can be guided by the electrical wave fields to appropriate spots within one or more channels. Alternatively, selected components may be guided to channels filled with specific binding pair members, such as antigen-antibodies, reactive with given substances of interest being moved in the medium or moved into contact with complementary components having a label or other member of a signal producing system of other types of chemicals for any number of purposes such as various transformations that are either physical or chemical in nature. Furthermore, bacterial or mammalian cells, or viruses may be sorted by complicated microfluidic networks in connection with a plurality of electrodes capable of generating electrical potentials of a variety of different strengths in order to move the cells or viruses through the fields based on the size, charge or shape of the particular material being moved. Separated cells or viruses may be analyzed or modified subsequently. For example, cell fractionation is possible by employing solid-phase extraction materials, including paramagnetic beads, non-magnetic particles, or the like, to specifically bind with the desired cells such that the bead-cell complex can be separated from the other cells. Cell lysis is then possible for releasing the intracellular materials for further analysis.

Microfluidic processing—processing carried out on a microfluidic scale. The processing involves fluid handling, transport and manipulation within chambers and channels of capillary dimension. Valveless sample injection is achieved by moving fluid from the reagent reservoirs into cross-channel injection zones, where plugs of buffer or test compounds are precisely metered and dispensed into a desired flowpath. The rate and timing of movement of the fluids in the various microchannels can be controlled by electrokinetic, magnetic, pneumatic, and/or thermal-gradient driven transport, among others. These sample manipulation methods enable the profile and volume of the fluid plug to be controlled over a range of sizes with high reproducibility. In addition, microfluidic processing may include sample preparation and isolation where enrichment microchannels containing separation media are employed for target capture and purification. Microfluidic processing may also include reagent mixing, reaction/incubation, separations and sample detection and analyses.

Sample—a medium containing a substance of interest, synthetic or natural, to be examined, treated, determined or otherwise processed. Typical sources for biological samples include body fluids such as, for example, whole blood, blood fractions such as serum and plasma, synovial fluid, cerebrospinal fluid, amniotic fluid, semen, cervical mucus, sputum, saliva, gingival fluid, urine, and the like. In addition, sample includes combinatorial chemistry generated libraries of compounds, usually small molecules, oligonucleotides and peptides. Other sources of samples are aqueous or water soluble solutions of natural or synthetic compounds, particularly, compounds that are potential therapeutic drugs where it is desired to determine if the compound binds to a specific receptor.

The amount of the sample depends on the nature of the sample and the nature of the processing to be conducted. For fluid samples such as whole blood, saliva, urine and the like the amount of the sample is usually about 1 to 1000 nanoliters, more usually, about 10 to 100 nanoliters. The sample can be pretreated and can be prepared in any convenient medium, which does not interfere with a microfluidic process in accordance with the present invention. An aqueous medium is preferred.

Substance of interest—the substance can be comprised of a member of a specific binding pair (sbp) and may be a ligand, which is monovalent (monoepitopic) or polyvalent (polyepitopic), synthetic or natural, antigenic or haptenic, and is a single compound or plurality of compounds which share at least one common epitopic or determinant site. The substance of interest can be a part of a cell such as bacteria or a cell bearing a blood group antigen such as A, B, D, etc., or an HLA antigen, or cell membrane receptors, or a microorganism, e.g., bacterium, fungus, protozoan, or virus.

The monoepitopic ligands will generally be from about 100 to 2,000 molecular weight, more usually from 125 to 1,000 molecular weight. The substances of interest include drugs, potential drug candidates, metabolites, pesticides, pollutants, and the like. The polyvalent ligands will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like. For the most part, the polyepitopic ligands to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

For receptors, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be 10⁶ or higher molecular weight, including such materials as avidin, DNA, RNA, thyroxine binding globulin, thyroxine binding prealbumin, transcortin, etc.

Also included are polynucleotides such as m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

Member of a specific binding pair ("sbp" member)—one of two different molecules having an area on the surface or in a cavity that specifically binds to and is therefore defined as complementary with a particular spatial and polar organization of the other molecule. The members of the sbp can be referred to as ligand and receptor such as members of an immunological pair, e.g., antigen-antibody. Complementary sbp members bind to one another, as for example, a ligand and its complementary receptor. With respect to two complementary sbp members, one may be referred to as the "binding partner" for the other. Sbp members can be immunological pairs such as antigen and antibody, or non-immunological pairs such as avidin and biotin. Sbp members can also be small molecules or residues of small molecules and their receptors. Small molecules have a molecular weight of from 100–2000, preferably 150–1000, and a receptor for the small molecule either exists or can be prepared. Examples of small molecules include derivatives of biotin, lysergic acid, fluorescein or a fluorescein derivative, and vitamin B12, with the corresponding receptors being avidin or streptavidin, anti-lysergic acid, anti-fluorescein and intrinsic factor, respectively.

Ligand—any organic compound for which a receptor naturally exists or can be prepared.

Receptor ("antiligand")—any compound or composition capable of recognizing a particular spatial and polar organization of a molecule, e.g., epitopic or determinant site. Illustrative receptors include membrane bound receptors such as G-protein receptors (e.g., muscarinic, adrenergic, prostaglandin and dopamine such as the D2 receptor), tyrosine kinase (insulin-like IGF, epidermal EGF, nerve NGF, fibroblast FGF growth factors), ion channels, T-cell receptors, the interleukins, and other naturally occurring receptors, e.g., thyroxine binding globulin, antibodies, enzymes, Fab fragments, lectins, nucleic acids, protein A, complement component Clq, and the like.

Label or reporter molecule—a chemical entity capable of being detected by a suitable detection means, including, but not limited to, spectrophotometric, chemiluminescent, electrochemical or radiochemical means. The reporter molecule can be conjugated to another molecule such as an sbp member, e.g., a ligand or an antibody, by procedures well known in the art. Typically, the reporter molecule contains a functional group suitable for attachment to the sbp member. The functional groups suitable for attaching the reporter group are usually activated esters or alkylating agents. Details of techniques for attaching reporter groups are well known in the art. See, for example, Matthews, et al., Anal. Biochem. (1985) 151:205–209 and Engelhardt, et al., European Patent Application No. 0302175.

Reporter molecules are members of a signal producing system capable of being detected directly or through a specific binding reaction to produce a detectable signal. The reporter molecule can be isotopic or nonisotopic, usually nonisotopic, and can be a catalyst, dye, fluorescent molecule, chemiluminescent molecule, coenzyme, enzyme, substrate, radioactive group, certain particles such as carbon and the like.

Antibody—an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgGl, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular molecule is maintained.

Signal producing system ("sps")—one or more components, at least one component being a detectable label or reporter molecule, which generate a detectable signal that relates to the amount of bound and/or unbound label, i.e., the amount of label bound or not bound to the compound being detected. The label and optionally other sps members are bound to an sbp member. Preferably, the label is an enzyme, electroluminescent group such as a transition metal complex (see, e.g., U.S. Pat. Nos. 5,541,113, 5,610,017, 5,527,710, 5,591,581, the relevant disclosures of which are incorporated herein by reference, chemiluminescer, fluorescer, radiolabel, or the like. Thus, with the above labels the signal is preferably detected and/or measured by detecting enzyme activity, luminescence, light emissions, or radioactivity, respectively. The labels and other reagents of the signal producing system must be stable at the temperatures used in the electroseparation method and subsequent assay.

Suitable labels include, by way of illustration and not limitation, enzymes such as alkaline phosphatase, glucose-6-phosphate dehydrogenase ("G6PDH") and horseradish peroxidase; promoters; dyes; fluorescers, such as fluorescein, isothiocyanate, rhodamine compounds, phycoerythrin, phycocyanin, allophycocyanin, o-phthaldehyde, and fluorescamine; electroluminescent labels such as ruthenium chelates; chemiluminescers such as isoluminol; sensitizers; coenzymes; enzyme substrates; radiolabels such as 125I, 131I, 14C, 3H, 57Co and 75Se. Suitable enzymes and coenzymes are disclosed in Litman, et al., U.S. Pat. No. 4,275,149, columns 19–28, and Boguslaski, et al., U.S. Pat. No. 4,318,980, columns 10–14; suitable fluorescers and chemiluminescers are disclosed in Litman, et al., U.S. Pat. No. 4,275,149, at columns 30 and 31; which are incorporated herein by reference.

Some labels can directly produce a signal, and therefore, additional components are not required to produce a signal. Numerous organic molecules, for example fluorescers, are able to absorb ultraviolet and visible light, where the light absorption excites these molecules to an excited energy state. This absorbed energy is then dissipated by emission of light at a second wavelength. Other labels that directly produce a signal include radioactive isotopes and dyes.

Alternately, the label may need other components to produce a signal. In this situation the signal producing system would then include all the components required to produce a measurable signal. These components may include substrates, electron transfer agents, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al. U.S. Pat. No. 5,185,243, columns 11–13, incorporated herein by reference.

The label can be bound covalently to numerous sbp members: an antibody; a receptor for an antibody; a receptor that is capable of binding to a small molecule conjugated to an antibody, a ligand analog, an oligonucleotide and the like. Bonding of the label to the sbp member may be accomplished by chemical reactions that result in replacing a hydrogen atom of the label with a bond to the sbp member or may include a linking group between the label and the sbp member. Other sps members may also be bound covalently to sbp members such as avidin-biotin, fluorescein-anti-fluorescein, and the like. Two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art. See for example, Rubenstein, et al., and U.S. Pat. No. 3,817,837, incorporated herein by reference. Alternatively, one label may be bound to a particle and a second label bound to a sbp member that binds to the sbp member attached to the particle.

Assay—a method for determining a substance capable of binding to a specific binding pair member, for example, for determining an analyte or detecting the degree of binding of a compound to a receptor. The determination may be qualitative or quantitative. Such assays depend on specific binding of a ligand to its receptor and include receptor binding assays, immunoassays, ligand/binding assays, polynucleotide assays, particularly polynucleotide hybridization assays, and cell surface binding assays. The assays may be utilized for drug discovery and screening, studies of receptors, detection of drugs and other substances, DNA detection, DNA sequencing, genetic analysis, monitoring of gene expression, and so forth.

Receptor-ligand binding competitive binding assays are a useful preliminary means for screening a large number of compounds for their therapeutic potential. Improved high throughput bioanalytical techniques are needed for characterizing the functional properties of receptor-mediated signaling and other cell transduction mechanisms. The receptor binding assays routinely arise in the fields of pharmacology, neurobiology, cardiology, immunology, microbiology and oncology, among others.

Heterogeneous assay—an assay wherein free labeled species is separated from a labeled species that is bound to another species such as an sbp member. The separation may be carried out by physical separation, e.g., by transferring one of the species to another reaction vessel, filtration, centrifugation, chromatography, solid phase capture, magnetic separation, and so forth and may include one or more washing steps. The separation may be nonphysical in that no transfer of one or both of the species is conducted, but the species are separated from one another in situ. In the heterogeneous assay the activity of a label is not affected by the reaction of specific binding pair members with one another. Regardless of the means of separation, the signal from the label may be measured from one or both of the separated species.

Homogeneous assay—an assay wherein free labeled species is not separated from a labeled species that is bound to another species such as an sbp member. The signal from the label is significantly different between the free labeled species and that which is bound and, thus, can be measured without separation.

Immunoassay—a specific binding assay in which the reagents include an antibody.

Figure 2:
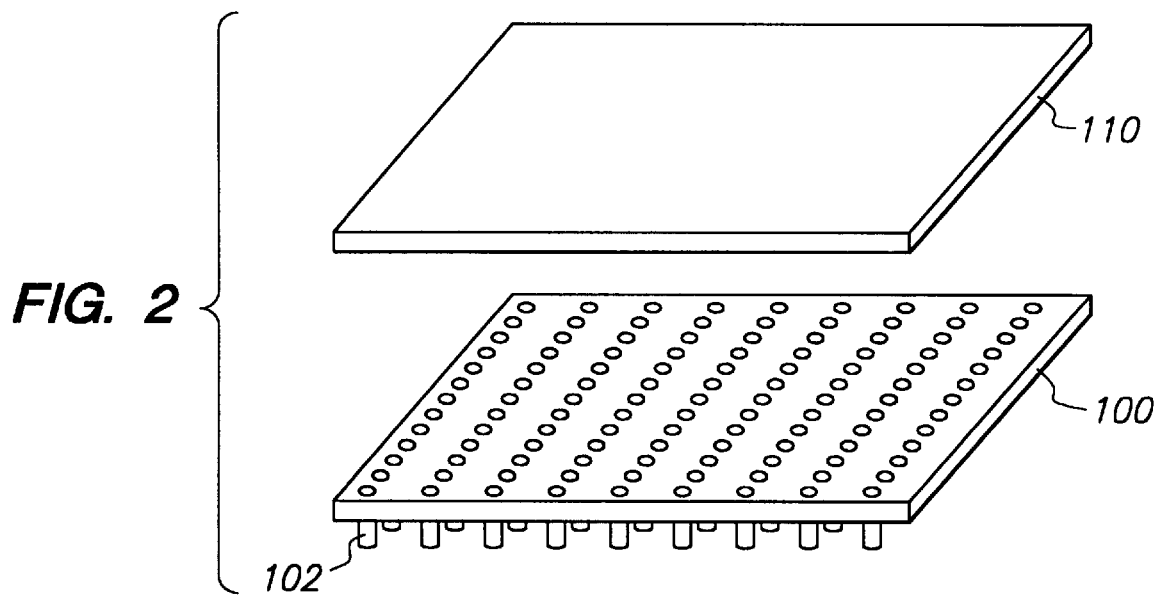
FIG. 2 is an exploded view of the apparatus of FIG. 1.

An embodiment of the present invention is depicted in FIGS. 1 and 2 by way of illustration and not limitation. The apparatus comprises first plate 100 that has an array of sample receiving elements 102 for receiving a plurality of samples from an array of sample containers. In the embodiment shown each of sample receiving elements 102 is capillary. The inarray of sample receiving elements 102 may be aligned so that they correspond with wells of a multiwell plate that contain samples. When the elements 102 are in the sample, an aliquot of sample is transferred to the element. For capillaries, transfer is conveniently by capillary action. The samples in sample receiving elements 102 can be manipulated and presented for simultaneous transfer to input reservoir 142 for microfluidic processing.

The volume of sample drawn into the capillary is controlled by the length and the bore diameter of the capillary. Typically, the bore diameter will be several hundred microns and the length of the capillary could range up to 10–20 mm. Such capillaries of these dimensions can fill with sample volumes in the 1 to 10 $\mu$L range. The volume of fluid drawn into the capillary can be controlled by carefully defining the bore diameter of the capillary and by defining the length of the capillary. The latter dimension can be defined by positioning a stop junction along the inner wall of the capillary. This stop junction could be an abrupt increase in the bore diameter of the capillary.

Alliteratively, using the techniques describe above, only a defined length of the inner wall of the capillary could be made sufficiently hydrophilic to draw in aqueous sample by capillary action; the boundary between the hydrophilic and hydrophobic surfaces of the inner wall would thus define stop junction.

The configuration of the capillaries conforms to the spacing format of the wells in the well plate. The capillaries can be constructed by any number of means. A major requirement is that the capillaries must be sufficiently hydrophilic to draw in several microliters of liquid sample by capillary action. A suitable capillary can be constructed from glass or silica tubing of appropriate dimensions. Alternatively, a suitable capillary can be constructed from a plastic material such as polyethylene, polypropylene, polycarbonate, polysulfone, polymethylmethacrylate, etc. In the case of capillaries constructed from plastic materials, however, the inner bore of the plastic capillary must be treated in some way to make the inner walls of the capillary sufficiently hydrophilic to draw in the sample by capillary action.

Appropriate treatments for altering the normally hydrophobic surface of the plastic and imparting hydrophilicity to the inner walls of the capillaries include coating the walls with a surfactant or wetting agent, grafting a layer of hydrophilic polymer onto the wall of the hydrophobic capillary or treating the walls of the capillary by plasma etching.

In one embodiment sample receiving elements 102 are sipper capillaries as disclosed in U.S. Pat. No. 5,560,811, at column 9, line 53, to column 10, line 45, the disclosure of which is incorporated herein by reference. In this approach first plate 100 has an array of sample receiving elements that comprise sample handling wells with a corresponding array of sipper capillaries. The array of sipper capillaries is aligned with wells of a multiwell plate containing the samples. When the sipper capillaries are in the sample, an aliquot of sample is transferred to the sipper capillary by wicking action. The samples in the capillaries can be manipulated to be presented to the microfluidic networks in second plate 110.

In this embodiment first plate 100 may also comprise a matrix element 104, which is typically made of a wide variety of porous matrix materials. For most applications, the porous matrix materials should have little or no affinity for sample. Useful porous matrix materials include membrane materials such as regenerated cellulose, cellulose acetate, polysulfone, polyvinylidine fluoride, polycarbonate and the like. For DNA samples, a cellulose acetate membrane such as that available from Amicon is useful. For protein samples, a membrane composed of polysulfone such as those available from Amicon or Gelman is useful.

Alternatively, porous matrix 104 could be a porous cylindrical or spherical plug of sintered polymer particles. Such porous materials are available from Porex or Interflow and are typically comprised of a bed of small polymeric particles that have been fused together by heat and pressure (sintering) to form a porous plug of predefined geometry. In another implementation, porous matrix 104 may comprise an ultrafiltration membrane with a defined molecular weight cut off. Alternatively, porous matrix 104 could be derivatized with some biochemical agent to impart a selective binding capability to matrix 104.

Figure 3:
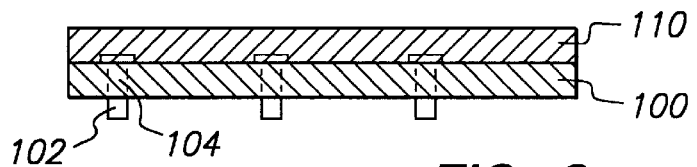
FIG. 3 is a cross-sectional view of the apparatus of FIG. 1 taken along lines 3—3.

The apparatus shown in FIGS. 1–3 also comprises a second plate 110 that is integral with the first plate. Second plate 110 comprises a planar array of microfluidic networks 108 having interconnected cavity structures 142 and channels 120 and 124 (see FIG. 4). Each of the microfluidic networks corresponds to a respective sample receiving element 102. In the embodiment shown in FIGS. 1–3, the capillaries are adapted for fluid communication with cavity structure 142. Liquid is transferred from sample receiving element 102 to cavity structure 142 by, for example, application of negative pressure, thermal gradient and the like. The capillary may have a fritted element disposed therein such that capillary flow will continue until the fritted element is saturated whereupon capillary draw ceases. Transfer of the liquid can then be effected such as described above.

In an embodiment wherein sample receiving elements 102 are sipper capillaries in accordance with U.S. Pat. No. 5,560,811, the apparatus also includes a means of fluid communication between plates 100 and 110. Such means of fluid communication includes, for example, a capillary between the two plates to provide for flow from the sample receiving well to the microfluidic networks of second plate 110. The capillary may extend from the sample receiving well to a cavity structure of the corresponding microfluidic network. The means of fluid communication may also be an opening in a cover plate for the second plate 110 where the opening permits liquid from the sample receiving well to be transferred mechanically, electrically, including electrostatically and piezoelectrically, or the like into a corresponding microfluidic network of second plate 110.

The microfluidic network has interconnected cavity structures and channels, the latter forming one or more flowpaths resulting in an interconnected system. In general, there is a main flowpath and one or more secondary flowpaths. A desired microfluidic process may be carried out in the main flowpath or in one of the secondary flowpaths. The additional flowpaths may be employed for a variety of purposes such as, for example, enrichment of a sample, isolation, purification, dilution, mixing, metering, and the like. A variety of configurations are possible, such as a branched configuration in which a plurality of flowpaths is in fluid communication with the main flowpath. See, for example, U.S. Pat. No. 5,126,022.

The main flowpath has associated with it at least one pair of electrodes for applying an electric field to the medium present in the flowpath. Where a single pair of electrodes is employed, typically one member of the pair is present at each end of the pathway. Where convenient, a plurality of electrodes may be associated with the flowpath, as described in U.S. Pat. No. 5,126,022, the relevant disclosure of which is herein incorporated by reference, where the plurality of electrodes can provide for precise movement of entities along the flowpath. The electrodes employed in the subject invention may be any convenient type capable of applying an appropriate electric field to the medium present in the flowpath with which they are associated.

Figure 4:
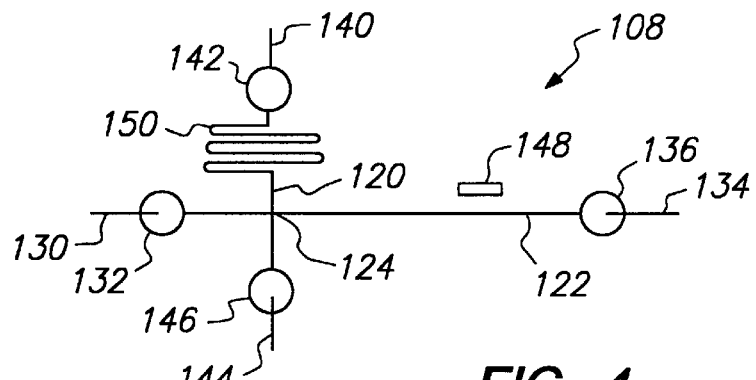
FIG. 4 is a perspective view of an embodiment of a microfluidic network.

An example of a basic configuration of a microfluidic network is shown in FIG. 4. Plate 110 is comprised of a plurality of microfluidic networks 108. Each network comprises main flowpath 120 and secondary flowpath 122, which intersect at 124. Electrode 130 is connected to reservoir 132 and electrode 134 is connected to reservoir 136. An electric potential can be applied to flowpath 122 by means of electrodes 130 and 134. Electrode 140 is connected to sample introduction port and reservoir 142 and electrode 144 is connected to reservoir 146. An electric potential can be applied to main flowpath 120 by means of electrodes 140 and 144. The main flowpath 120 has optional portion 150 that is tortuous to provide an appropriate path length and residence time to achieve mixing by diffusion, incubation, and so forth.

Secondary flowpath 122 has detection zone 148 where the result of a microfluidic process may be detected. For example, if the microfluidic process is an assay for an analyte, the detection zone permits the detection of a signal produced during the assay. Alternatively, if the microfluidic process is a chemical synthesis, the detection zone may be used to detect the presence of the synthesized compound. It is, of course, within the purview of the present invention to utilize several detection zones depending on the nature of the microfluidic process. There may be any number of detection zones associated with a single channel or with multiple channels. Suitable detectors for use in the detection zones include, by way of example, photomultiplier tubes, photodiodes, photodiode arrays, avalanche photodiodes, linear and array charge coupled device (CCD) chips, CCD camera modules, spectrophotometers, spectrofluorometers, and the like. Excitation sources include, for example, filtered lamps, LED's, laser diodes, gas, liquid and solid state lasers, and so forth. The detection may be laser scanned excitation, CCD camera detection, coaxial fiber optics, confocal back or forward fluorescence detection in single or array configurations, and the like.

Detection may be by any of the known methods associated with the analysis of capillary electrophoresis columns including the methods shown in U.S. Pat. Nos. 5,560,811 (column 11, lines 19–30), 4,675,300 and 5,324,401, the relevant disclosures of which are incorporated herein by reference. An example of an optical system for reading the channels in the detection zones comprises a power supply, which energizes a photomultiplier tube. A power supply energizes a 75 watt Xenon lamp. Light from the lamp is condensed by focusing lens, which passes light to an excitation filter. A dichroic mirror directs excitation light to a microscope. The apparatus is mounted on a so that light passes over the channels. Fluorescent emission light is collected by the microscope, passed through a dichroic mirror, emission filter, or spatial filter before reaching the photomultiplier (PMT). The output signal of PMT is fed to an analog-to-digital converter, which in turn is connected to computer.

Alternatively, a static detection system in which a stationary detection point some distance from the injection end of the capillary is monitored as bands to be analyzed traverse the length of the capillary and pass by the detection zone could be used. This type of detection could be implemented using optical fibers and lenses to deliver the excitation radiation to the capillary and to collect the fluorescent emission radiation from the detection zone in the capillary. Appropriate multiplexing and demultiplexing protocols might be used to sequentially irradiate and monitor a large array of capillaries using a single source and a single or a small number of photodetectors. Using this approach, each capillary in the array is sequentially polled to detect any analyte band in the detection zone of that capillary.

The detectors may be part of an instrument into which the present apparatus is inserted. The instrument may be the same instrument that comprises the electrode leads and other components necessary for utilizing the present apparatus. However, separate instruments may be used for housing a sample container plate, incubation of sample and reagents, detection of a result, electrical field application, and other operations such as temperature and humidity control, and so forth. Humidity control may be achieved in a number of ways such as, for example, the use of humidistats, water vapor sources confined in the device in fluid communication with other areas thereof, and so forth. Other methods of humidity control will be evident to those skilled in the art.

Generally, prior to using a microfluidic network a suitable electroflow medium as described above is introduced into the flowpaths defined by the channels in the secondary plate. The medium may be conveniently introduced through one of the reservoirs at the termini of each of the channels or directly into the channels themselves prior to sealing of a cover plate to the planar substrate.

The use of a microfluidic network is next discussed with reference to FIG. 4. Sample is introduced into sample introduction port and reservoir 142 together with appropriate reagents for carrying out a microfluidic process. An electric potential is applied across electrodes 140 and 144 causing medium containing the sample and other reagents to move through flowpath 120 and, in particular, portion 150 of 120. Mixing of sample and reagents, as well as incubation, take place in portion 150. When the portion of the medium containing the sample and reagents reaches intersection 124, the electric potential applied between electrodes 140 and 144 is discontinued and an electric potential is applied between electrodes 130 and 134. The point at which the sample and other reagents reach intersection 124 may be determined by detecting the presence of the sample or one of the reagents directly or by empirically determining the time at which the sample and reagents should reach the intersection 124, based on the particular nature of the sample, the medium employed, the strength of the electric potential and so forth. Application of the electrical potential to electrodes 130 and 134 causes a plug of medium of precise amount (determined by the dimensions of the channel) to move along secondary flowpath 122 towards reservoir 136 and through detection zone 148 where detection is conducted. This is the basic manner in which an exemplary microfluidic network operates. Of course, as will be appreciated by one of ordinary skill in the art, the precise manner of operation of microfluidic networks in an apparatus in accordance with the present invention is dependent on the construction of the apparatus.

Considerations include, for example, whether reagents are present on board the apparatus or added from a source outside the apparatus. Other considerations include manipulation of beads or magnetic beads in the channels, filling of channels with buffer, manipulation of discrete drops within otherwise unfilled channels, method of fluid movement (electroosmotic, electrokinetic, surface tension, centrifugal, pneumatic), mixing two or more reagents, incubation, and so forth.

Those skilled in the electrophoresis arts will recognize a wide range of electric potentials or field strengths may be used, for example, fields of 10 to 1000 V/cm are used with 200–600 V/cm being more typical. The upper voltage limit for commercial systems is 30 kV, with a capillary length of 40–60 cm, giving a maximum field of about 600 V/cm. There are reports of very high held strengths (2500–5000 V/cm) with short, small bore (10 microns) capillaries micro machined into an insulating substrate. Normal polarity is to have the injection end of the capillary at a positive potential. The electroosmotic flow is normally toward the cathode. Hence, with normal polarity all positive ions and many negative ions will run away from the injection end. Generally, the "end capillary" detector will be near the cathode.

The polarity may be reversed for strongly negative ions so that they run against the electroosmotic flow. For DNA, typically the capillary is coated to reduce electroosmotic flow, and the injection end of the capillary is maintained at a negative potential.

Figure 5:
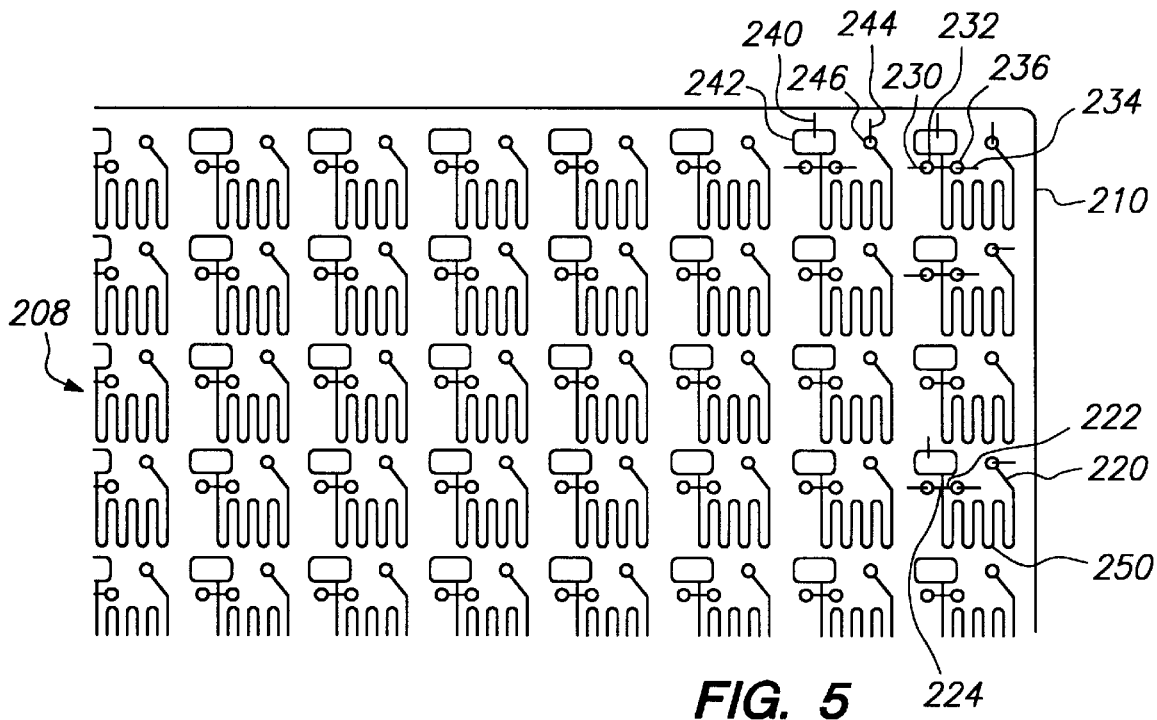
FIG. 5 is a perspective view of one embodiment of a portion of a plate having a plurality of microfluidic networks.
Figure 6:
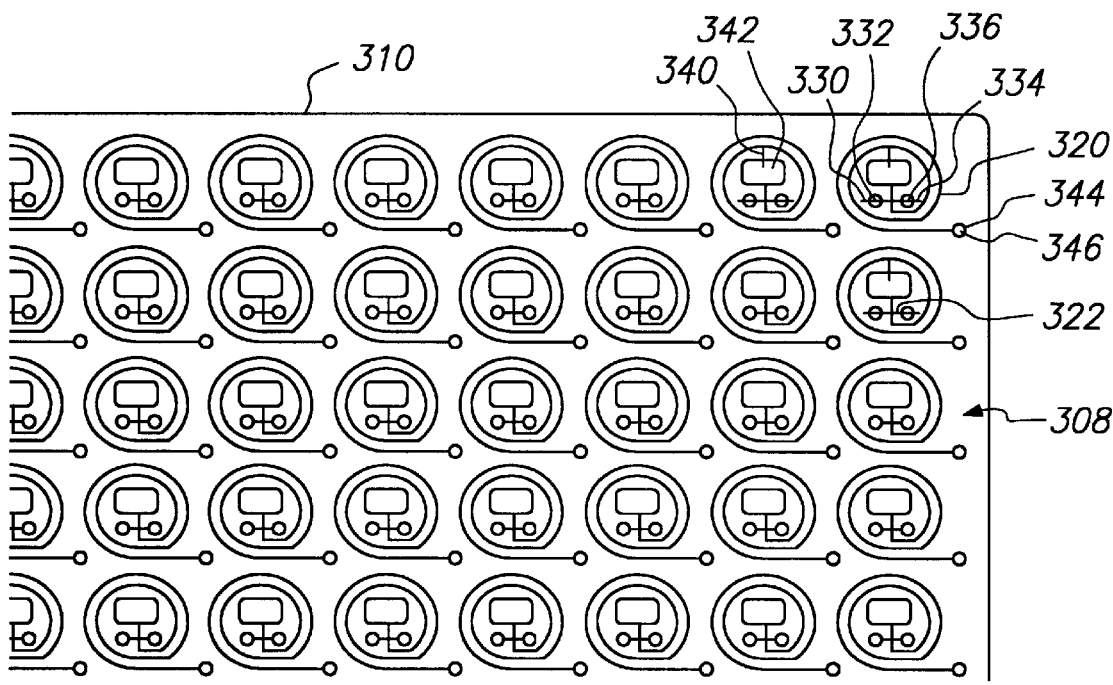
FIG. 6 is a perspective view of another embodiment of a portion of a plate having a plurality of microfluidic networks.
Figure 7:
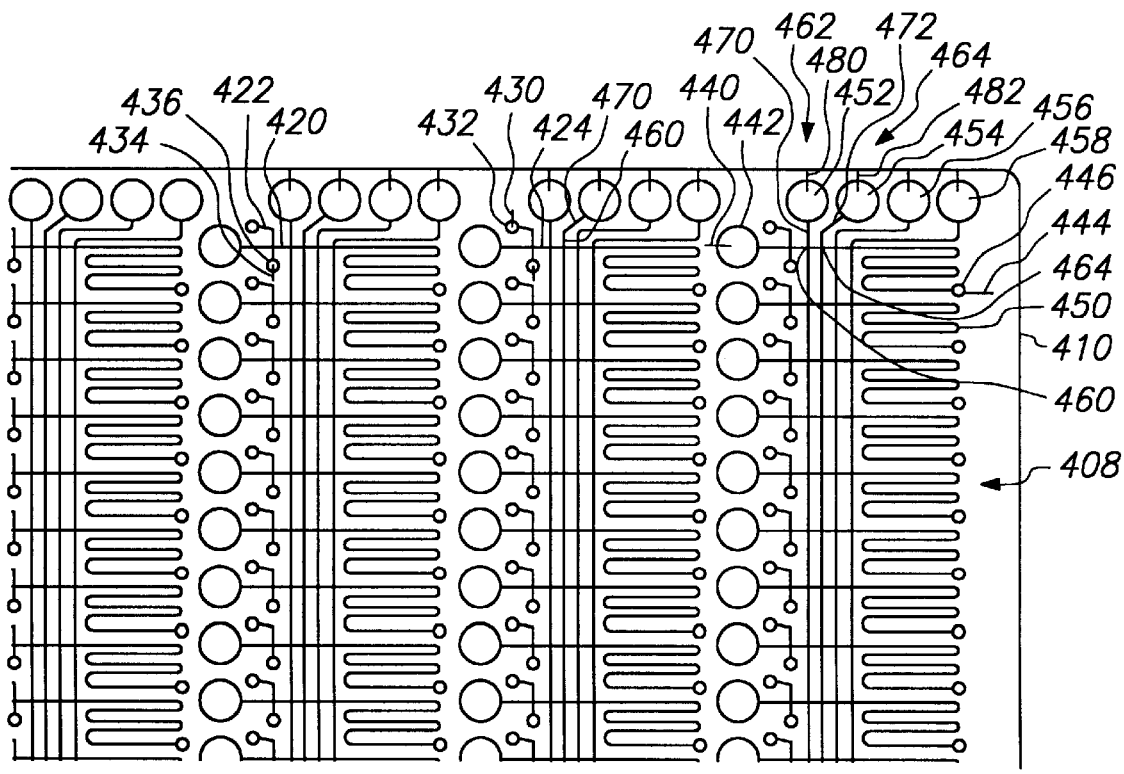
FIG. 7 is a perspective view of another embodiment of a portion of a plate having a plurality of microfluidic networks.

Examples of devices that are suitable for the second plate in the above-integrated apparatus are provided in FIGS. 5–7. Only a portion of the microfluidic network plates is shown in FIGS. 5–7. It is to be understood that the microfluidic network plates may have any number of separate networks including more than or less than 96. The number of microfluidic networks may be multiples of 96 where the number is greater than 96 or multiples of 8 where the number is less than 96. In addition, some of the features of the microfluidic networks are not shown in all of the networks depicted in FIG. 5–7.

In FIG. 5 a portion of a plate 210 is shown where the plate may have up to ninety-six (96) microfluidic networks 208. Each network comprises main flowpath 220 and secondary flowpath 222, which intersect at 224. Electrode 230 is connected to reservoir 232 and electrode 234 is connected to reservoir 236. An electric potential can be applied to secondary flowpath 222 by means of electrodes 230 and 234. Electrode 240 is connected to sample introduction port and reservoir 242 and electrode 244 is connected to reservoir 246. An electric potential can be applied to main flowpath 220 by means of electrodes 240 and 244. The main flowpath 220 has a portion 250 that is in the form of a linear reciprocating coil to provide a tortuous path.

In FIG. 6 a portion of a plate 310 is shown where the plate may have up to ninety-six (96) microfluidic networks 308. Each network comprises main flowpath 320 and secondary flowpath 322, which intersect at 324. Electrode 330 is connected to reservoir 332 and electrode 334 is connected to reservoir 336. An electric potential can be applied to secondary flowpath 322 by means of electrodes 330 and 334. Electrode 340 is connected to sample introduction port and reservoir 342 and electrode 344 is connected to reservoir 346. An electric potential can be applied to main flowpath 320 by means of electrodes 340 and 344. The main flowpath 320 is a circular coil to provide a tortuous path.

In FIG. 7 a portion of a plate 410 is shown where the plate may have up to ninety-six (96) microfluidic networks 408. Each network comprises main flowpath 420 and secondary flowpath 422, which intersect at 424. Electrode 430 is connected to reservoir 432 and electrode 434 is connected to reservoir 436. An electric potential can be applied to secondary flowpath 422 by means of electrodes 430 and 434. Electrode 440 is connected to sample introduction port and reservoir 442 and electrode 444 is connected to reservoir 446. An electric potential can be applied to main flowpath 420 by means of electrodes 440 and 444. The main flowpath 420 has a portion 450 that is in the form of a linear reciprocating coil to provide a tortuous path. The microfluidic networks of plate of FIG. 6 also comprise set of reagent reservoirs 452, 454, 456 and 458. Each of the reagent reservoirs has a channel providing communication between the reagent reservoir and each of the main flowpaths of the microfluidic networks. Accordingly, reagent reservoir 452 has a channel 470 that intersects main flowpath 420 at 460 for each of the microfluidic networks in row 462 of plate 410. Likewise, reagent reservoir 454 has a channel 472 that intersects main flowpath 420 at 464 for each of the microfluidic networks in row 464 of plate 410. The same situation exists for reagent reservoirs 456 and 458. Reagents are moved through channels 470 and 472 by means of application of electric potential at electrodes 480 and 482, respectively. By appropriate alternation of electric potential in channels 470 and 472 on the one hand and main channel 420 on the other, precise amounts of reagents can be metered into main flowpath 420.

With regard to electrodes, some or all of the electrodes may be within the second plate with external connections to power supplies that may be part of an instrument into which the present apparatus is inserted. On the other hand, some or all of the electrodes might be on a separate part (e.g. built into an instrument into which the present apparatus is inserted), such that the electrodes can be immersed into the appropriate fluid reservoirs at the time of use. In this approach the electrodes in the separate instrument may be adapted to make contact with an appropriate lead from each of the reservoirs forming a part of the microfluidic networks in the subject apparatus. The electrodes may be strip metal electrodes formed in a stamping process or chemical etching process. The electrodes may be wires or strips either soldered or glued with epoxy and can be made of conductive materials such as platinum, gold, carbon fibers and the like. The electrodes could be deposited, coated or plated onto a section of the exterior wall of a capillary near each end of the capillary. Controlled vapor deposition of gold, platinum, or palladium metal onto the exterior wall of the capillary is one method of forming the electrodes. This technique can be used to produce an electrode layer with a thickness up to several microns. Thicker electrodes could be subsequently formed by electrochemically plating gold, palladium or platinum onto the thin electrode formed by the vapor deposition process. Electrodes could be integral with the second plate formed by silk screening process, printing, vapor position, electrodeless plating process, etc. Carbon paste, conductive ink, and the like could be used to form the electrode.

Regardless of the embodiment of the present invention that is constructed, it is preferable for the electrodes to be connected to an electronic computer. The computer has programmed software dedicated to providing the moving waves or voltage profile along the channel. Various different types of software can be provided so as to obtain the best possible results in the particular microfluidic processing conducted.

It is also within the purview of the present invention that the computer software that is connected to the electrodes be made interactive with an optical detection device such as ultraviolet or fluorescence spectrometer. The spectrometer can be focused singly or at various points along the medium in the channels. As the ultraviolet spectrometer reads different types of substances being moved to different portions of the medium, the information can be sent to the computer, which can adjust the speed of the waves or voltage distribution profiles being generated in order to more precisely fine tune the resolution of the substances being moved through the medium.

As mentioned above, the channels can be in any shape. More specifically the channels can be fashioned so that it has a plurality of branches. Each of the branches along with the channel itself can be filled with a desired medium. Various reagents may be moved along the branches by utilizing the moving electric wave generated by the computer. Accordingly, a sophisticated computer program may be utilized to provide for various protocols for microfluidic processing such as chemical synthesis, sequencing of polynucleotides.

The integrated apparatus of the present invention may have any convenient configuration capable of comprising the first and second plates and their respective component parts. The cavities and channels of the second plate are usually present on the surface of a planar substrate where the substrate will usually, though not necessarily be covered with a cover plate to seal the microfluidic networks present on the surface of the planar substrate from the environment. The cover plate will have appropriate communication means for establishing communication between each of the sample receiving elements of the first plate and the corresponding microfluidic network of the second plate. Such means include, for example, through-holes, capillaries, porous wicks and the like. The apparatus may have a variety of configurations such as, for example, rectangular, circular, or other convenient configuration. Generally, apparatus in accordance with the present invention are of a size that is readily handled and manipulated. In general, a rectangular apparatus has dimensions of about 3 inches by 5 inches; a circular apparatus has a diameter of about 4 to 16 inches; and each would have a thickness of about 0.60 to 1.5 inches (including all of the elements of the apparatus). It should be obvious that the size of the present devices and apparatus is not critical and is in general a function of the particular multiwell plate with which the present device may be used.

The apparatus may be fabricated from a wide variety of materials, including glass, silica, quartz, ceramics and polymers, including elastomeric material, thermosets and thermoplastics, e.g., acrylics, and the like. The various components of the apparatus may be fabricated from the same or different materials, depending on a number of factors such as, e.g., the particular use of the device, the economic concerns, solvent compatibility, optical clarity, color, mechanical strength, dielectric properties, e.g., dielectric strength greater than 100 V/cm, and so forth. For example, the planar substrate of the second plate may be fabricated from the same material as the cover plate, e.g., polymethylmethacrylate, or from different materials such as, e.g., polymethylacrylate for the substrate and glass for the cover plate. Likewise, the first plate may be fabricated from the same material as the second plate, or one of the components of the second plate, e.g., glass bottom, glass top; plastic bottom, plastic cover, or from different materials such as, e.g., glass for the first plate and plastic for the second plate.

For applications where it is desired to have a disposable integrated device, due to ease of manufacture and cost of materials, the device typically is fabricated from a plastic. For ease of detection and fabrication, the entire apparatus may be fabricated from a plastic material that is optically transparent, which generally allows light of wavelengths ranging from 180 to 1500 nm, usually 220 to 800 nm, more usually 450 to 700 nm, to have low transmission losses. Suitable materials include fused silica, plastics, quartz, glass, and so forth.

Also of interest as materials suitable for fabrication of one or more components of the present apparatus are plastics having low surface charge under conditions or electroflow. Particular plastics finding use include polymethyl methacrylate, polymethyl acrylate, polycarbonate, polyethylene terephthlate, polystyrene or styrene copolymers, polyesters, and the like.

The apparatus may be fabricated using any convenient means, including conventional molding and casting techniques, extrusion sheet forming, calendaring, thermoforming, and the like. For example, with apparatus prepared from a plastic material, a silica mold master, which is negative for the network structure in the planar substrate of the second plate, can be prepared by etching or laser micromachining. In addition to having a raised ridge that forms the channel in the substrate, the silica mold may have a raised area that provides for one or more cavity structures in the planar substrate. Next, a polymer precursor formulation can be thermally cured or photopolymerized between the silica master and support planar plate, such as a glass plate. Where convenient, the procedures described in U.S. Pat. No. 5,110,514, the relevant disclosure of which is incorporated by reference, may be employed. After the planar substrate has been fabricated, electrodes may be introduced where desired.

For the second plate cavity structures or reservoirs may be formed by boring holes only part way through the substrate at the ends of the channels, so that the cavity structures are not open on the opposite surface of the second plate. Holes can be bored or cut through the cover and aligned with the cavity structures. Liquids can be added to cavity structures formed in this manner can be filled through holes in the cover, rather than from the opposite side.

The substrate for the second plate may take a variety of shapes such as, for example, disk-like, card-like, and may be a layered or laminated sandwich structure. The substrate for the second plate is usually about 1 µm thick, usually at least about 5 µm, and more usually at least about 50 µm thick, where the thickness may be as great as 5 mm or greater.

As mentioned above, the second plate may be constructed from two or more parts, usually two parts, e.g., a base plate and a cover plate. Each part generally has a planar surface and the parts are sealed together so that the planar surfaces are opposed. The planar surface of the base plate usually includes one or more cavity structures and channels, while the planar surface of the cover plate may or may not include one or more cavity structures and channels.

The cover plate is usually placed over, and sealed to, the surface of the substrate of the base plate. The cover plate may be sealed to the substrate using any convenient means, including ultrasonic welding, adhesives, etc. The cover may be a more or less rigid plate, or it may be a film, and the thickness of the cover may be different for materials having different mechanical properties. Usually the cover ranges in thickness from at least about 200 µm, more usually at least about 500 µm, to as thick as usually about 5 mm or thicker, more usually about 2 mm. The cover substrate may be fabricated from a single material or be fabricated as a composite material. In some instances the cover is of a plastic material, and it may be rigid or elastomeric.

In one approach the apparatus may have multiple layers that are sandwiched together similar to multiple layer electronic printed circuit boards. In this approach the apparatus may be made in a manner similar to the printed circuit boards. Each layer contains cavities, channels and through-holes. When the various plates are assembled into an apparatus, the channels and through-holes in each layer can interconnect forming three dimensional fluid circuits. This approach allows significantly greater circuit complexity and circuit density than the single layer approach.

Another approach for the transfer of liquids from the first plate to the second plate of the present apparatus involves a plurality of active liquid transfer elements corresponding to each well of a multiwell plate. Upon activation of the active liquid transfer elements, an amount of liquid from the well of the well plate is actively transferred to a microfluidic network of the second plate through a corresponding through hole in the second plate. Exemplary of active liquid transfer elements include capillary droplet ejectors that are driven mechanically, electrically, pneumatically, thermally, and so forth, and capillary forces and surface tension, hydrodynamics, and the like.

Figure 8:
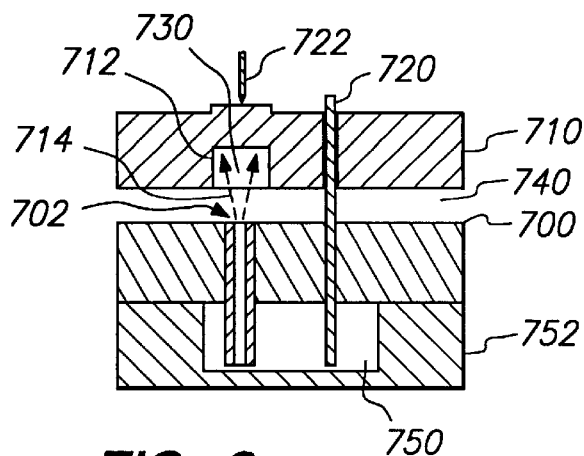
FIG. 8 is a cross-sectional view of one embodiment of an assembly depicting means of transferring liquid from a sample container to a sample receiving element.
Figure 9:
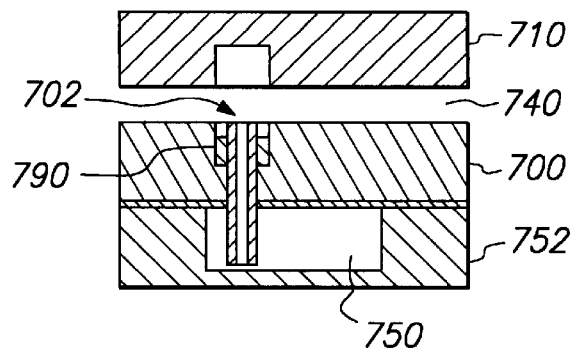
FIG. 9 is a cross-sectional view of another embodiment of an assembly depicting means of transferring liquid from a sample container to a sample receiving element.

An example of this particular embodiment is depicted in FIGS. 8 and 9 by way of example and not limitation. The apparatus in FIG. 8 comprises first plate 700 and second plate 710. The first plate 700 that has an array of sample receiving elements 702 in the form of capillaries for taking up a plurality of samples from an array of sample containers. The array of capillaries is aligned so that they correspond with wells 750 of a multiwell plate 752 that contain samples. When the capillaries 702 are in the sample, an aliquot of sample is transferred to capillary 702 by means of capillary action. Transfer of this aliquot to a microfluidic network 712 of the second plate is realized by applying an electrical potential using electrodes 720 and 722. When the electrical potential is applied, a pulse of liquid 714, which is a precise amount of the sample, is sprayed into a sample receiving reservoir 730 of the microfluidic network. The electrical potential applied is on the same order of magnitude as that described above to achieve electroflow. Usually, the electrical potential is about 100 V/cm to 5 kV/cm, preferably about 250 V/cm to 500 V/cm.

In the embodiment shown in FIG. 8 second plate 710 is secured above first plate 700 so that a space generally designated 740 lies in between. The space 740 is usually about 0.5 to 3 mm. The apparatus of FIG. 8 may be constructed so as to achieve the spatial relationship between plates 700 and 710. Spacer elements may be employed in the manufacture of the apparatus. The apparatus may also be designed to be assembled by the user into an integral device prior to contact with a multiwell plate. Various interlocking means may be utilized to secure second plate 710 to first plate 700. Such means include, for example, tongue and groove, or post and pit alignment with elastomeric gaskets or clamps, integral molded spring clips, and the like.

Alternatively, plate 710 can be separate from plate 700 in the device of FIG. 8. In this approach plate 710 is positioned, by some mechanical or electromechanical means, above plate 700, which is first positioned above multiwell plate 752. Liquid is then transferred from multiwell plate 752 to sample receiving reservoir 730. After the transfer is complete, plate 710 can be moved away and further processing of the liquid can be carried out in the microfluidic networks of plate 710.

Other examples of various means for achieving liquid transfer from a capillary to a microfluidic network in the second plate are depicted in FIGS. 9–12. As mentioned above, such means may be provided as a separate part, along with other parts, of an apparatus in accordance with the present invention. These parts may be assembled by the user. In this way flexibility is achieved in that intermediate plates may also be included between the first and second plates. Such intermediate plates include, for example, a plate with filters spaced apart corresponding to the sample receiving elements. Thus, the user would have the ability to carry out manipulations other than sample transfer such as a filtration of the sample and the like. It is also within the purview of the present invention to include such intermediate plates as an integral part of the present apparatus. In the embodiment of FIG. 8 such intermediate plate would be found in space 740.

Figure 10:
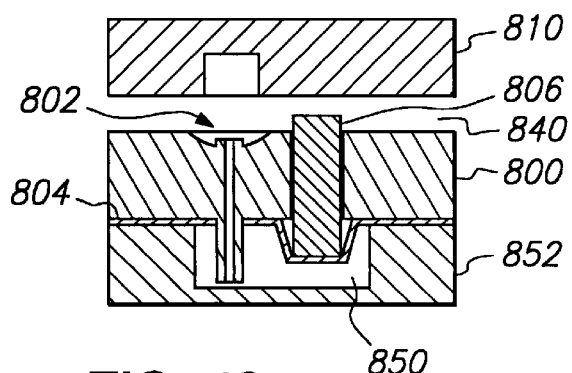
FIG. 10 is a cross-sectional view of another embodiment of an assembly depicting means of transferring liquid from a sample container to a sample receiving element.

Another point to be mentioned, using the embodiment of FIG. 10 by way of illustration and not limitation, is that first plate 700 as a separate plate from second plate 710 can be used to transfer liquids to a plate other than one containing microfluidic networks. Separate first plate 700 can be employed to transfer samples to a planar surface in the form of an array of spots on which chemical synthesis or analysis can be conducted. As will be appreciated, first plates in FIGS. 9–12 below can also be used separately in this fashion.

Another point to be mentioned is that simultaneous transfer of liquids may be achieved to less than all of the wells in a multiwell plate by independently controlling the activating means such as the electrodes, plunger, heater elements, pneumatic drive and so forth in each of these respective embodiments. Thus, if one wished to transfer liquids to 16 wells of a 96 well plate, these 16 wells would have an activation means independent from that for the remaining wells.

The apparatus of FIG. 9 is similar to that in FIG. 8 except that piezoelectric collar 790 is present in place of the electrodes of FIG. 8. The pulse of liquid is generated by piezoelectric collar 790. The piezoelectric collar 790, when actuated, rapidly constricts the capillary near the upper end resulting in the release of liquid in the capillary.

Referring to FIG. 10, the apparatus comprises first plate 800 and second plate 810. First plate 800 includes sealing membrane 804 through which a plurality of capillaries 802 extends. First plate 800 also includes a plurality of plungers 806 that are slidably positioned in first plate 800. Each of the plungers are situated near a respective capillary. Second plate 810 is secured above first plate 800 in a biased relationship so that second plate 810 may be reciprocally moved in the direction of first plate 800. In this way plungers 806 may be simultaneously depressed by depressing plate 810. To this end the space 840 between the first and second plates may contain suitable biasing elements such as springs, elastomeric substances, e.g., polydimethyl siloxane (PDMS), and so forth. When the plungers 806 are depressed, a pulse of liquid from well 850 in multiwell plate 852, which is a precise amount of the sample, is sprayed into a sample receiving reservoir 830 of the microfluidic network in second plate 810.

Figure 11:
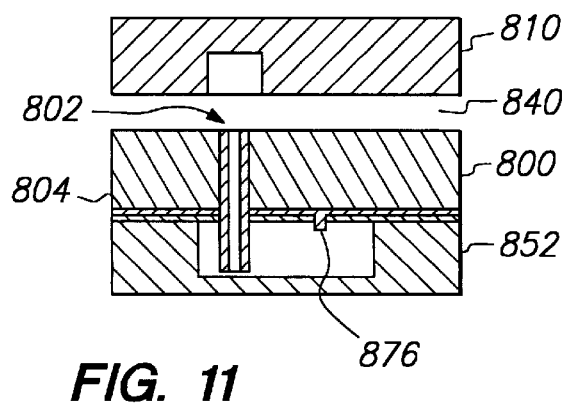
FIG. 11 is a cross-sectional view of another embodiment of an assembly depicting means of transferring liquid from a sample container to a sample receiving element.
Figure 12:
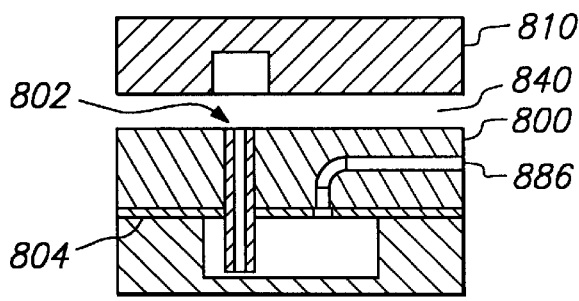
FIG. 12 is a cross-sectional view of another embodiment of an assembly depicting means of transferring liquid from a sample container to a sample receiving element.

The alternative embodiments depicted in FIGS. 11 and 12 utilize heat from heater 876 and compressed gas from tube 886, respectively, in place of the pressure achieved with plunger 806 of FIG. 10.

Another aspect of the present invention comprises kits for processing a sample. In one embodiment a kit comprises an apparatus as described above and reagents, other than reagents within the apparatus, for processing a sample. The reagents for the kits may be packaged in the same or separate containers, so that the concentration of the reagents provides for substantial optimization of the method and assay. The reagents may each be in separate containers or various reagents can be combined in one or more containers depending on the cross-reactivity and stability of the reagents. Under appropriate circumstances one or more of the reagents in the kit can be provided as a dry powder, usually lyophilized, including excipients, which on dissolution will provide for a reagent solution having the appropriate concentration for performing a method or assay in accordance with the present invention. The kit can also include additional reagents depending on the nature of the method for which the kit is used. For example, the kit may include solid phase extraction materials including paramagnetic beads and non-magnetic particles, lysis solutions, wash and elution and running buffers, biomolecular recognition elements including receptors, enzymes, antibodies and other specific binding pair members, labeling solutions, substrates, reporter molecules, sample purification materials including membranes, beads, and the like, and so forth.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An apparatus for conducting a microfluidic process, said apparatus comprising:
   (a) a first plate comprising an array of sample receiving elements adapted for receiving a plurality of samples from an array of sample containers and dispensing said samples and
   (b) a second plate integral with said first plate for receiving said dispensed samples, said second plate comprising a planar array of microfluidic networks of cavity structures and channels for conducting a microfluidic process.

2. An apparatus for conducting a microfluidic process, said apparatus comprising:
   (a) a first plate comprising an array of sample receiving elements adapted for receiving a plurality of samples from an array of sample wells and
   (b) a second plate integral with said first plate, said second plate comprising a planar array of microfluidic networks of cavity structures and channels for conducting a microfluidic process wherein each of said microfluidic networks is adapted for fluid communication with a corresponding sample receiving element of said first plate.

3. The apparatus of claim 2 wherein each of said sample receiving elements comprises a sample handling well that is in fluid communication with a corresponding capillary adapted to receive sample from one of said sample wells.

4. The apparatus of claim 2 wherein said array of sample wells conforms to the format of a 96, 192, 384 or 1536 well plate.

5. The apparatus of claim 2 wherein each of said microfluidic networks comprises:
   (a) a sample receiving cavity structure adapted for receiving sample from said corresponding sample receiving element and
   (b) one or more additional cavity structures in fluid communication with said sample receiving cavity structure.

6. The apparatus of claim 2 wherein each of said microfluidic networks comprises:
   (a) a sample receiving cavity structure adapted for receiving sample from said corresponding sample receiving element,
   (b) one or more waste cavity structures in capillary communication with said sample receiving cavity structure,
   (c) one or more buffer containing structures in capillary communication with said sample receiving cavity structure.

7. The apparatus of claim 6 wherein each of said microfluidic networks of cavity structures and channels comprises a tortuous path.

8. A kit comprising in packaged combination:
   (a) the apparatus of claim 1 and
   (b) reagents, other than reagents within said apparatus, for processing a sample.

9. The kit of claim 8 wherein said reagents are selected from the group consisting of solid phase extraction materials, lysis solutions, wash and elution and buffers, specific binding pair members, labeling solutions, substrates, reporter molecules, sample purification materials.

10. A method for processing an array of samples, said method comprising:
   (a) simultaneously transferring at least a portion of each sample in an array of sample wells to a corresponding array of sample receiving elements that are part of a first plate comprising an array of sample receiving elements adapted for receiving a plurality of samples from an array of sample wells,
   (b) simultaneously transferring at least a portion of each sample from said sample receiving elements to a corresponding array of microfluidic networks that is part of a second plate integral with said first plate, said second plate comprising a planar array of microfluidic networks of cavity structures and channels for conducting a microfluidic process wherein each of said microfluidic networks is adapted for fluid communication with a corresponding sample receiving element, and
   (c) processing said array of samples.

11. The method of claim 10 wherein said processing comprises conducting an analysis of said samples.

12. The method of claim 10 wherein said processing comprises conducting a chemical synthesis.

13. The method of claim 10 wherein each of said sample receiving elements comprises a sample handling well that is in fluid communication with a corresponding capillary adapted to receive sample from one of said sample wells.

14. The method of claim 10 wherein said array of sample wells conforms to the format of a 96, 192, 384 or 1536 well plate.

15. The method of claim 10 wherein each of said microfluidic networks comprises:
   (a) a sample receiving cavity structure adapted for receiving sample from said corresponding sample receiving element and
   (b) one or more additional cavity structures in fluid communication with said sample receiving cavity structure.

16. The method of claim 10 wherein each of said microfluidic networks comprises:
   (a) a sample receiving cavity structure adapted for receiving sample from said corresponding sample receiving element,
   (b) one or more waste cavity structures in capillary communication with said sample receiving cavity structure,
   (c) one or more buffer containing structures in capillary communication with said sample receiving cavity structure.

17. The method of claim 10 wherein each of said microfluidic networks of interconnected cavity structures and channels of capillary dimension comprises a tortuous path.

* * * * *

Adverse Decisions in Interference

Patent No. 6,103,199, Torleif Ove Bjornson, Randy M. McCormick, David S. Soane, CAPILLARY ELECTROFLOW APPARATUS AND METHOD, Interference No. 105,444, final judgment adverse to the patentees rendered February 27, 2007, as to claims 1-17.

*(Official Gazette April 17, 2007)*